US006934355B2

(12) United States Patent
Dolazza et al.

(10) Patent No.: US 6,934,355 B2
(45) Date of Patent: Aug. 23, 2005

(54) METHOD OF AND SYSTEM FOR DECREASING X-RAY EXPOSURE TIMES IN FULL FIELD DIGITAL MAMMOGRAPHY

(75) Inventors: Enrico Dolazza, Boston, MA (US); Oscar Khutoryansky, Newton, MA (US)

(73) Assignee: Analogic Corporation, Peabody, MA (US)

( * ) Notice: Subject to any disclaimer, the term of this patent is extended or adjusted under 35 U.S.C. 154(b) by 21 days.

(21) Appl. No.: 10/753,920

(22) Filed: Jan. 7, 2004

(65) Prior Publication Data

US 2005/0147205 A1 Jul. 7, 2005

(51) Int. Cl.⁷ .............................................. A61B 6/04
(52) U.S. Cl. ........................................ 378/37; 378/62
(58) Field of Search ..................... 378/37, 62, 98.6, 378/98.8

(56) References Cited

U.S. PATENT DOCUMENTS 6,483,891 B1 * 11/2002 Lazarev et al. ............... 378/37
6,862,337 B2 * 3/2005 Claus et al. .................. 378/26

* cited by examiner

Primary Examiner—Edward J. Glick
Assistant Examiner—Elizabeth Keaney
(74) Attorney, Agent, or Firm—McDermott Will & Emery LLP

(57) ABSTRACT

A method of and system for decreasing X-ray exposure time in a full field digital mammography (FFDM) system is designed so that the size of the focal spot image in the image plane is dimensioned as a function of the linear size of the pixel of the digital detector of the detector array and of the geometrical magnification factor of the focal spot so that the modular transfer function is limited only by the pixel size.

25 Claims, 2 Drawing Sheets

METHOD OF AND SYSTEM FOR DECREASING X-RAY EXPOSURE TIMES IN FULL FIELD DIGITAL MAMMOGRAPHY

CROSS-REFERENCE TO RELATED APPLICATIONS

Not Applicable

STATEMENT REGARDING FEDERALLY SPONSORED RESEARCH

Not Applicable

REFERENCE TO MICROFICHE APPENDIX

Not Applicable

BACKGROUND OF THE DISCLOSURE

The present invention relates to digital imaging, and more particularly, to a system for and method of reducing x-ray exposure time of normal examination procedures, i.e. of those procedures that do not use magnification geometry, performed with digital mammographic equipment.

The focal spot of a radiography system is the linear dimension of the ortho-normal projection on the image plane of the region of the x-ray source, that is the area of the anode, that radiates photons. Typically, the focal spot of currently available, film-based mammography systems has two nominal sizes: 0.3 mm, for use in normal examinations; and 0.1 mm, for use in magnification procedures. The reason for maintaining a relatively small focal spot in normal mammographic examinations performed with film-based equipment is to prevent further loss of image resolution in the range of spatial frequencies of diagnostic interest (typically between 1 and 5 lp/mm), such a loss being beyond the loss of resolution caused by the finite thickness of the scintillating material of the film/screen detector. On the other hand, it is well known that a small focal spot size results in long exposure times, because the photon flux from the x-ray source is a strong function of the focal spot size; thus a small focal spot results in low x-ray flux.

A long exposure time, in turn, results in various negative effects, the most important of which is an increased probability that the breast under examination could move during the exposure, so that its image is smeared and therefore diagnostically unacceptable. Another reason to keep the exposure time as short as possible is to minimize the time during which the breast of the patient is painfully compressed. This approach, however, is relevant only when the reduction of the exposure time results in a significant reduction of the time during which the breast is under compression. Current generation, digital mammography equipment has critically adopted the same small focal spot size used in film-based systems. This, in turn, necessitates a relatively long exposure time, that is in the range 0.5 to 4.0 seconds depending on the beam quality and the breast thickness, whilst it is common experience that when the duration of the exposure exceeds 2 seconds, the probability of breast motion becomes significant. It is desirable to substantially reduce the x-ray exposure time of normal breast examination (i.e. the term "normal examination" is intended to mean examination that does not use magnification geometry where the image is projected to be larger than the original object) using digital mammography systems.

SUMMARY OF THE INVENTION

A digital mammography x-ray system and method is disclosed. The system and method are designed to decrease X-ray exposure time in a full field digital mammography (FFDM) system. Specifically, the size of the focal spot image in the image plane is dimensioned as a function of the linear size of the pixel of the digital detector of the detector array and of the geometrical magnification factor of the focal spot so that the modular transfer function is limited only by the pixel size.

In accordance with one aspect, the system comprises:
an x-ray source for providing a focal spot; and
a plurality of digital detectors, each defining a pixel spaced from the focal spot so as to define (a) a geometrical demagnification factor of the focal spot and (b) an image plane, wherein each detector has an upper limit resolution defined by its modular transfer function, related to the spatial frequency response of the detector geometry;
wherein the size of the focal spot image in the image plane is dimensioned as a function of the linear size of the pixel of the digital detector and of the geometrical magnification factor of the focal spot so that the modular transfer function is limited only by the pixel size.

In accordance with another aspect, the system comprises:
a digital detector array for receiving X-ray energy and producing an image therefrom, wherein the digital detector array includes a plurality of individual detectors, each characterized by a pixel size P; and,
an X-ray source for generating the X-ray energy, wherein the X-ray source includes a focal spot;
wherein the system produces a focal spot image on the digital detector array is characterized by a size that is between about one half of and twice the pixel size P.

In accordance with another aspect, the a digital mammography x-ray apparatus comprises:
an x-ray source for providing a focal spot; and
a plurality of digital detectors, each defining a pixel spaced from the focal spot so as to define (a) a geometrical magnification factor of the focal spot and (b) an image plane;
wherein the size of the focal spot image in the image plane is a function of the linear size of the pixel of the digital detector and of the geometrical magnification factor of the focal spot, wherein:
the focal spot image is between a size of the order of 0.5 PD/d and 2.0 PD/d;
wherein P is the linear size of the pixel,
D is the distance between the focal spot and a plane of the object to be imaged, and
d is the distance between the plane of the object to be imaged and the detector plane.

Various embodiments include: the size of the pixel is small enough to prevent serious degradation of the spatial frequencies of diagnostic interest that are typically in the frequency band between approximately 1 lp/mm and approximately 5 lp/mm; the detectors are selenium-based; the detectors are provided in the form of a digital detector array wherein each of the plurality of individual detectors is characterized by a pixel size P of approximately 85 μm; the X-ray source has a focal spot size of at least 0.85 mm and less than or equal to 1.70 mm; and the ratio of D/d is at least 20.

In accordance with another aspect, a method of decreasing X-ray exposure time in a full field digital mammography system, comprises:

generating x-rays from the focal spot of an x-ray source toward a plurality of digital detectors, each defining a pixel spaced from the focal spot so as to define (a) a geometrical demagnification factor of the focal spot and (b) an image plane, wherein each detector has an upper limit resolution defined by its modular transfer function, related to the spatial frequency response of the detector geometry such that the size of the focal spot image in the image plane is dimensioned as a function of the linear size of the pixel of the digital detector and of the geometrical magnification factor of the focal spot so that the modular transfer function is limited only by the pixel size.

In accordance with yet another aspect, a method of decreasing X-ray exposure time in a full field digital mammography system, comprising:

generating x-ray energy from a focal spot of an X-ray source toward a digital detector array for receiving X-ray energy and producing an image therefrom, wherein the digital detector array includes a plurality of individual detectors, each characterized by a pixel size P so that the a focal spot image produced on the digital detector array is characterized by a size that is between about one half of and twice the pixel size P.

In accordance with yet another aspect, a method comprises:

generating x-rays from a focal spot of an x-ray source toward a plurality of digital detectors, each defining a pixel spaced from the focal spot so as to define (a) a geometrical magnification factor of the focal spot and (b) an image plane, wherein the size of the focal spot image in the image plane is a function of the linear size of the pixel of the digital detector and of the geometrical magnification factor of the focal spot, wherein:

the focal spot image is between a size of the order of 0.5 PD/d and 2.0 PD/d;

wherein P is the linear size of the pixel,

D is the distance between the focal spot and a plane of the object to be imaged, and d is the distance between the plane of the object to be imaged and the detector plane.

Various embodiments of the method include: the size of the pixel is small enough relative to the size of the focal spot so as to prevent serious degradation of the spatial frequencies of diagnostic interest that are typically in the frequency band between approximately 1 lp/mm and approximately 5 lp/mm; the ratio of D/d is at least 20; each detector is characterized by a pixel size P of approximately 85 µm; and the X-ray source has a focal spot size of at least 0.85 mm and less than or equal to 1.70 mm.

BRIEF DESCRIPTION OF DRAWINGS

The foregoing and other objects of this invention, the various features thereof, as well as the invention itself, may be more fully understood from the following description, when read together with the accompanying drawings in which.

DESCRIPTION OF THE PREFERRED EMBODIMENTS

The finite pixel size of a digital detector of a digital mammography system poses an intrinsic limit to the resolution of any image created by the system. A detector with a pixel size P has an upper limit resolution defined by its modular transfer function MTF, related to the spatial frequency response of the detector geometry, i.e., $$MTF(f) \leq sinc(\pi Pf) \tag{1}$$

This limitation does not significantly affect the diagnostic conspicuity of the image when the size of the pixel is small enough to prevent serious degradation of the spatial frequencies of diagnostic interest that are typically in the frequency band between approximately 1 lp/mm and approximately 5 lp/mm. Further, digital detectors are deemed to provide superior image quality compared to film/screen detectors, because in the above mentioned frequency band of interest they feature higher Detective Quantum Efficiency (DQE) and higher Modulation Transfer Function (MTF). The latter is especially significant for direct conversion digital detectors, for example, like those based upon selenium.

Figure 1:
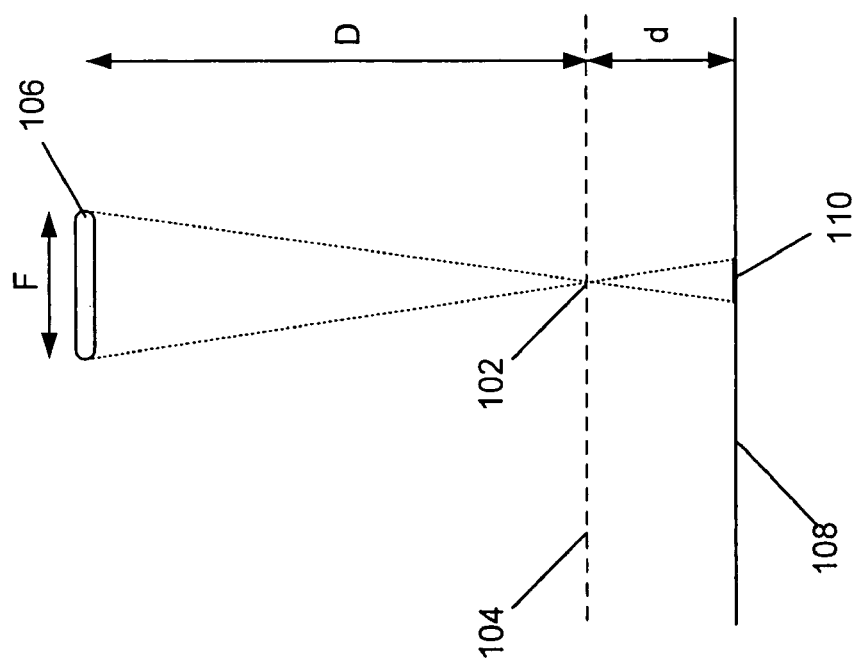
FIG. 1 shows, shows a schematic diagram of how the finite size F of the focal spot affects the upper limit resolution of the mammography system; and, FIG. 2 shows a schematic diagram of one preferred embodiment of an apparatus for decreasing X-ray exposure time in a full field digital mammography system

The finite size F of the focal spot 106 affects the upper limit resolution of the mammography system, as shown in the diagram of FIG. 1. A point 102 (e.g., a pin-hole), located on a plane 104 (e.g., an examination plane) at a distance D from the focal spot 106 and a distance d from the detector plane 108, is projected as an image 110 on the detector. The size of the focal spot 106 as projected is de-magnified by the distance ratio D/d. D/d is typically of the order of 20 when the mammography system is used to perform a normal examination, which during typical use is in the great majority of the cases. The combined effect of the finite size Fd/D of the focal spot projection on the detector plane and that of the finite size P of the detector pixel is measured by their convolution function. In terms of spatial frequencies, the upper limit resolution becomes:

$$MTF(f) \leq sinc(\pi fP) \cdot sinc(\pi fFd/D) \tag{2}$$

Equation (2) implies that the resolution of a digital mammography system remains practically limited only by the pixel geometry up to a size of the focal spot image of the order of one half the pixel size, i.e., for F≤PD/2d. As the size of the focal spot image increases beyond this value, the resolution then gradually decreases or degrades, to be completely dominated by the size of the focal spot when its image on the detector plane exceeds twice the size of the pixel. For a pixel size of 0.085 mm and the value of D/d=20, typical for a normal examination, the resolution of the system is practically limited only by the pixel geometry if the focal spot does not exceed 0.85 mm. Although some further limited increase of the focal spot size, i.e. up to F= PD/1.5d, would not theoretically result in a significant degradation of the system resolution, it is convenient to limit the size of the focal spot image on the detector plane to one half the pixel size. In fact, the focal spot is the ortho-normal projection of the x-ray source on the image plane, and therefore its projection will be wider on regions of the image that see the x-ray source under an angle different from 90 degrees. As an additional practical consideration, it is worth noticing that most x-ray tubes exhibit a focal spot wider than its nominal value, whereas in the text of the present disclosure it is assumed that the actual focal spot size is equal to its nominal value.

Figure 2:
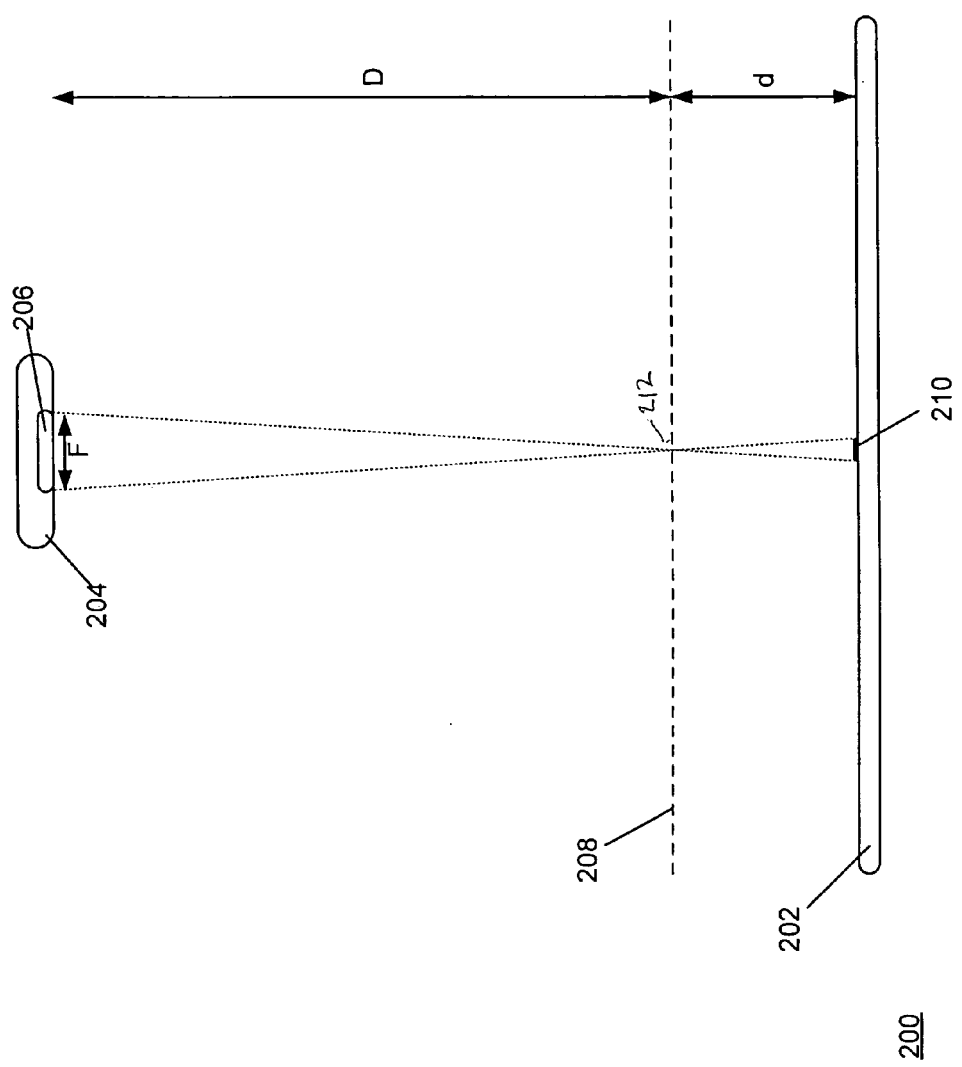

It should be appreciated that the system geometry described herein is for use in normal mammography examination, i.e., not for use in magnification procedures. In addition, FIG. 2 shows a schematic diagram of one preferred embodiment of an apparatus 200 for decreasing X-ray exposure time in a full-field, digital mammography system. For simplicity in describing the apparatus 200, other necessary components of the mammography system known to one skilled in the art are not shown. The apparatus 200 includes a digital detector array 202 including a plurality of individual detectors, each detector being characterized by a pixel size P. The individual detectors are preferably selenium based, although other detector compositions known in the art may also be used. The apparatus 200 also includes an X-ray source 204 for generating a beam of X-ray energy. The X-ray source 204 includes a focal spot 206, which is the specific region of the X-ray source 204 that radiates X-ray energy. The X-ray source 204 directs X-ray energy through an examination plane 208 and onto the detector array 202. The examination plane 208 is disposed substantially parallel to the detector array 202, at a first distance D from the X-ray source 204 and a second distance d from the detector array 202. For normal examination, the ratio D/d is approximately equal to 20. The apparatus 200 images the pinhole 212, which is located on the examination plane 208, into the focal spot image 210, having a size given by Fd/D, on the detector array 202. The size of the focal spot image 210 is preferably, although not necessarily, equal to P/2. Thus, the size (linear dimension) of the focal spot image is preferably, although not necessarily, equal to one half the size (linear dimension) of the detector pixel, which requires the focal spot size F to be equal to PD/2d. This example of focal spot size is preferable but it is not meant to be limiting. Other focal spot sizes may also be used to optimize various system parameters at the expense of other than optimal resolution results.

The main advantage of a larger focal spot as compared to that used in prior art mammography systems is that the larger focal spot provides higher x-ray flux from the x-ray tube, with a concomitant reduction of the examination time. The reduction in examination time results in a substantially lower opportunity for motion artifacts. To quantify the reduction of the examination time it should be noticed that the tube x-ray flux is approximately proportional to the area of the focal spot, and therefore to $F^2$. For example, in a system where the detector has a pixel size of 0.085 mm, and a system geometry in which the ratio D/d is about 20, if the linear dimension of the focal spot increases from 0.3 mm to 0.6 mm, a rather conservative value, the x-ray flux output by the tube increases by a factor of approximately 4, and the examination time decreases by the same factor. Thus, with a focal spot size of 0.6 mm, the examination time will be approximately ¼ of the examination time associated with a focal spot size of 0.3 mm. In practical terms, this means that the average mammography examination will have a duration of a fraction of a second and no examination will exceed 1 second. This is well below the time of about 2 seconds, which is considered a practical time threshold after which the probability of motion artifacts dramatically increases. A reduction of the examination time results in another advantage for digital mammography systems, whose detector array in general typically operates in interleaving fix time intervals during which x-rays can be fired (called exposure windows) with fix time intervals during which image data are read out. The duration of the exposure window is in general determined so as to accommodate the majority of the patient exposure times in one window only, and therefore the x-ray widow accounts for most of the cycle time. The average time delay between the exposure command, which is asynchronously issued with respect to the detector cycling, and the start of the actual x-ray exposure, is typically proportional to the detector cycle time. Therefore, a substantial reduction of actual exposure times, which will result in substantially shorter exposure windows, will also substantially reduce the exposure delay.

The increase of the focal spot size, and the related increase of x-ray tube output, is also very beneficial in connection with certain advanced mammographic procedures, especially those procedures in which image data are obtained through digital processing of multiple images taken at different directions of the x-ray beam in reference to the object under examination. One well-known example of such advanced procedures is tomosynthesis, for volume reconstruction of the breast tissues. A tomosynthesis acquisition takes several seconds, during which time a certain number of low dose images are taken with the x-ray tube radiating x-rays from different positions. According to the present state of the art, the tube moves through the various positions and stops when the x-rays are fired to prevent loss of resolution in the low dose images. This stop-and-go movement results in longer total acquisition time. At each stop, enough time must elapse before the image is taken to allow the mechanical vibration associated with the acceleration and deceleration of the tube to be sufficiently dampened to or below an acceptable level. An x-ray tube that provides an increased X-ray flux output because of a larger focal spot, allows acquisition of each of the low dose images in a few milliseconds. Therefore, such images can be taken while the tube is moved along a desired trajectory with a continuous motion, without significant loss of resolution. As a result the overall tomosynthesis acquisition becomes substantially shorter, with obvious benefits of decreased motion artifacts as well of a shorter compression time.

The invention may be embodied in other specific forms without departing from the spirit or essential characteristics thereof. The present embodiments are therefore to be considered as illustrative and not restrictive. The scope of the invention is indicated by the appended claims rather than by the foregoing description, and is intended to include and embrace any and all changes which come within the meaning and/or range of the equivalency of the claims.

What is claimed is:

1. A digital mammography x-ray apparatus comprising:
   an x-ray source for providing a focal spot; and
   a plurality of digital detectors, each defining a pixel spaced from the focal spot so as to define (a) a geometrical demagnification factor of the focal spot and (b) an image plane, wherein each detector has an upper limit resolution defined by its modular transfer function, related to the spatial frequency response of the detector geometry;
   wherein the size of the focal spot image in the image plane is dimensioned as a function of the linear size of the pixel of the digital detector and of the geometrical magnification factor of the focal spot so that the modular transfer function is limited only by the pixel size.

2. A digital mammography x-ray apparatus according to claim 1, wherein:
   the size of the pixel is small enough to prevent serious degradation of the spatial frequencies of diagnostic interest that are typically in the frequency band between approximately 1 lp/mm and approximately 5 lp/mm.

3. A digital mammography x-ray apparatus according to claim 1, wherein the detectors are selenium-based.

4. A digital mammography x-ray apparatus according to claim 1, wherein the detectors are provided in the form of a digital detector array wherein each of the plurality of individual detectors is characterized by a pixel size P of approximately 85 µm.

5. A digital mammography x-ray apparatus according to claim 1, wherein the X-ray source has a focal spot size of at least 0.85 mm and less than or equal to 1.70 mm.

6. A system for decreasing X-ray exposure time in a full field digital mammography system, comprising:
a digital detector array for receiving X-ray energy and producing an image therefrom, wherein the digital detector array includes a plurality of individual detectors, each characterized by a pixel size P; and,
an X-ray source for generating the X-ray energy, wherein the X-ray source includes a focal spot;
wherein the system produces a focal spot image on the digital detector array is characterized by a size that is between about one half of and twice the pixel size P.

7. A system according to claim 6, wherein:
the size of the pixel is small enough to prevent serious degradation of the spatial frequencies of diagnostic interest that are typically in the frequency band between approximately 1 lp/mm and approximately 5 lp/mm.

8. A system according to claim 6, wherein the detector array is selenium-based.

9. A system according to claim 6, wherein the detector array includes individual detectors that are each characterized by a pixel size P of approximately 85 µm.

10. A system according to claim 6, wherein the X-ray source has a focal spot size of at least 0.85 mm and less than or equal to 1.70 mm.

11. A digital mammography x-ray apparatus comprising:
an x-ray source for providing a focal spot; and
a plurality of digital detectors, each defining a pixel spaced from the focal spot so as to define (a) a geometrical magnification factor of the focal spot and (b) an image plane;
wherein the size of the focal spot image in the image plane is a function of the linear size of the pixel of the digital detector and of the geometrical magnification factor of the focal spot, wherein:
the focal spot image is between a size of the order of 0.5 PD/d and 2.0 PD/d;
wherein P is the linear size of the pixel,
D is the distance between the focal spot and a plane of the object to be imaged, and
d is the distance between the plane of the object to be imaged and the detector plane.

12. A digital mammography x-ray apparatus according to claim 11, wherein:
the size of the pixel is small enough to prevent serious degradation of the spatial frequencies of diagnostic interest that are typically in the frequency band between approximately 1 lp/mm and approximately 5 lp/mm.

13. A digital mammography x-ray apparatus according to claim 11, wherein the detectors are selenium-based.

14. A digital mammography x-ray apparatus according to claim 11, wherein the ratio of D/d is at least 20.

15. A digital mammography x-ray apparatus according to claim 11, wherein the detectors are provided in the form of a digital detector array wherein each of the plurality of individual detectors is characterized by a pixel size P of approximately 85 µm.

16. A digital mammography x-ray apparatus according to claim 11, wherein the X-ray source has a focal spot size of at least 0.85 mm and less than or equal to 1.70 mm.

17. A method of decreasing X-ray exposure time in a full field digital mammography system, comprising:
generating x-rays from the focal spot of an x-ray source toward a plurality of digital detectors, each defining a pixel spaced from the focal spot so as to define (a) a geometrical demagnification factor of the focal spot and (b) an image plane, wherein each detector has an upper limit resolution defined by its modular transfer function, related to the spatial frequency response of the detector geometry such that the size of the focal spot image in the image plane is dimensioned as a function of the linear size of the pixel of the digital detector and of the geometrical magnification factor of the focal spot so that the modular transfer function is limited only by the pixel size.

18. A method according to claim 17, wherein the size of the pixel is small enough relative to the size of the focal spot so as to prevent serious degradation of the spatial frequencies of diagnostic interest that are typically in the frequency band between approximately 1 lp/mm and approximately 5 lp/mm.

19. A method of decreasing X-ray exposure time in a full field digital mammography system, comprising:
generating x-ray energy from a focal spot of an X-ray source toward a digital detector array for receiving X-ray energy and producing an image therefrom, wherein the digital detector array includes a plurality of individual detectors, each characterized by a pixel size P so that the a focal spot image produced on the digital detector array is characterized by a size that is between about one half of and twice the pixel size P.

20. A method according to claim 19, wherein the size of the pixel is small enough to prevent serious degradation of the spatial frequencies of diagnostic interest that are typically in the frequency band between approximately 1 lp/mm and approximately 5 lp/mm.

21. A method comprising:
generating x-rays from a focal spot of an x-ray source toward a plurality of digital detectors, each defining a pixel spaced from the focal spot so as to define (a) a geometrical magnification factor of the focal spot and (b) an image plane, wherein the size of the focal spot image in the image plane is a function of the linear size of the pixel of the digital detector and of the geometrical magnification factor of the focal spot, wherein:
the focal spot image is between a size of the order of 0.5 PD/d and 2.0 PD/d;
wherein P is the linear size of the pixel,
D is the distance between the focal spot and a plane of the object to be imaged, and
d is the distance between the plane of the object to be imaged and the detector plane.

22. A method according to claim 21, wherein:
the size of the pixel is small enough to prevent serious degradation of the spatial frequencies of diagnostic interest that are typically in the frequency band between approximately 1 lp/mm and approximately 5 lp/mm.

23. A method according to claim 22, wherein the ratio of D/d is at least 20.

24. A method according to claim 21, wherein each detector is characterized by a pixel size P of approximately 85 µm.

25. A method according to claim 21, further including providing an X-ray source having a focal spot size of at least 0.85 mm and less than or equal to 1.70 mm.

* * * * *